United States Patent
Iles

(10) Patent No.: US 10,161,941 B2
(45) Date of Patent: Dec. 25, 2018

(54) RAPID SCREENING AND EVALUATION OF DIABETES AND PREDIABETES BY GLYCATED HEMOGLOBIN MASS SPECTROMETRY

(71) Applicant: Map IP Holding Limited, Cambridgeshire (GB)

(72) Inventor: Raymond Kruse Iles, Cambridgeshire (GB)

(73) Assignee: MAP IP Holding Limited, Ely (GB)

( * ) Notice: Subject to any disclaimer, the term of this patent is extended or adjusted under 35 U.S.C. 154(b) by 1 day.

(21) Appl. No.: 15/506,731

(22) PCT Filed: Aug. 27, 2015

(86) PCT No.: PCT/GB2015/052487
§ 371 (c)(1),
(2) Date: Feb. 25, 2017

(87) PCT Pub. No.: WO2016/030687
PCT Pub. Date: Mar. 3, 2016

(65) Prior Publication Data
US 2017/0254814 A1    Sep. 7, 2017

(30) Foreign Application Priority Data
Aug. 29, 2014   (GB) .................................. 1415369.6

(51) Int. Cl.
*G01N 33/48*    (2006.01)
*G01N 15/06*    (2006.01)
(Continued)

(52) U.S. Cl.
CPC ..... *G01N 33/6851* (2013.01); *G01N 33/6848* (2013.01); *G01N 33/723* (2013.01); *G01N 2800/042* (2013.01)

(58) Field of Classification Search
None
See application file for complete search history.

(56) References Cited

U.S. PATENT DOCUMENTS

| 4,847,209 | A | * | 7/1989 | Lewis | ................ | G01N 33/5306 |
| | | | | | | 422/417 |
| 2004/0171026 | A1 | * | 9/2004 | Hochstrasser | ..... | G01N 33/6896 |
| | | | | | | 435/6.11 |

(Continued)

FOREIGN PATENT DOCUMENTS

WO    2012166055    12/2012

OTHER PUBLICATIONS

Alqahtani, et al, "Use of Glycated Hemoglobin in the Diagnosis of Diabetes Mellitus and Pre-diabetes and Role of Fasting Plasma Glucose, Oral Glucose Tolerance Test," Sep. 2013, International Journal of Preventative Medicine, 4(9): 1025-1029.*

(Continued)

*Primary Examiner* — Jill A Warden
*Assistant Examiner* — Brittany I Fisher
(74) *Attorney, Agent, or Firm* — Stradley Ronon Stevens & Young, LLP

(57) ABSTRACT

The method describes rapid screening of whole blood samples, pin prick and blood spot cards, subjected to MALDI-ToF Mass spectrometry. The spectra is generated and compared to those from normal healthy controls. Characteristic spectra are indicative of the presence of a hemoglobinopathy and the method can be used to screen/diagnose all sickle cell diseases, alpha and beta Thalassemias.

15 Claims, 6 Drawing Sheets

(51) Int. Cl.
G01N 33/68 (2006.01)
G01N 33/72 (2006.01)

(56) References Cited

U.S. PATENT DOCUMENTS

| | | | |
|---|---|---|---|
| 2006/0020440 A1* | 1/2006 | Hellerstein | G01N 33/5088 703/11 |
| 2009/0093066 A1* | 4/2009 | Blackshear | C07K 9/001 436/501 |
| 2010/0184658 A1* | 7/2010 | Gelber | A61K 38/16 514/6.9 |
| 2010/0330594 A1* | 12/2010 | Hart | G01N 33/6893 435/7.25 |
| 2011/0053191 A1* | 3/2011 | Hess | G01N 33/689 435/7.92 |
| 2011/0250618 A1* | 10/2011 | Nelson | G01N 33/6893 435/7.21 |
| 2012/0107859 A1* | 5/2012 | Petrotchenko | C12Q 1/37 435/23 |

OTHER PUBLICATIONS

Bahar, Adele et al, "Relationship Between Beta-Globin Gene Carrier State and Insulin Resistance," 2012, Journal of Diabetes and Metabolic Disorders, 11:22, http://www.jdmdonline.com/content/11/1/22.*

Faynor, M Steven, "Clnical Pathology Rounds: Glycosylated Hemoglobin Electrophoresis," 1997, Laboratory Medicine, vol. 28, No. 6, pp. 370-373 (Year: 1997).*

Hattan, Stephen J., "Analysis and Quantitation of Glycated Hemoglobin by Matrix Assisted Laser Desorption/Ionizaiton Time of Flight Mass Spectrometry," Jan. 5, 2016, American Society for Mass Spectrometry, vol. 27, pp. 532-541 (Year: 2016).*

A. Biroccio et al., "A quantitative method for the analysis of glycated and glutathionylated hemoglobin by matrix-assisted laser desorption ionization-tme of flight mass spectrometry", Analytical Biochemistry, 2005, 336(2):279-288.

A. D'Alessandro et al., "Haemoglobin glycation (Hb1Ac) increases during red blood cell storage: a MALDI-TOF mass-spectrometry-based investigation", Vox Sanguinis, 2013, 105(2):177-180.

A. Lapolla et all, "A matrix-assisted laser desorption/ionization mass spectrometry study of the non-enzymatic glycation products of human globins in diabetes", Rapid Communications in Mass Spectrometry, 2005, 19(2):162-168.

A. Lapolla et al., "Protein glycation in diabetes as determined by mass spectrometry", International Journal of Endocrinology, 2013, 49(9):1399-1311.

Kleinert P., et al., "Mass Spectrometry: A Tool for Enhanced Detection of Hemoglobin Variants", 2007, Clinical Chemistry, 54(1), pp. 69-76.

Hanchani J., et al., "Maldi-TOF MS profiling as the first-tier screen for sickle cell disease in neonates: matching throughput to objectives", 2011, Proteomics-Clinical Applications, 5, pp. 7-8.

Zanella, I., et al., "Phenotype determination of hemoglobinopathies by mass spectrometry", 2009, Clinical Biochemistry, 42(18), pp. 1807-1817.

Troxler H., et al., "Advances in hemoglobinopathy detection and identification", 2002, Advances in Clinical Chemistry, 57, pp. 1-28.

* cited by examiner

Figure 5 - Summary table of spectra peak analysis 7500 to 8200 m/z and relative percentage abundance –

A) - Phenotypic abnormal blood samples

| Assigned Peak | m/z | Cntrl-1 | Cntrl-2 | Cntrl-3 | Cntrl-4 | Cntrl-5 | Cntrl-6 | Cntrl-7 | Cntrl-8 | Cntrl-9 | Average | SD |
|---|---|---|---|---|---|---|---|---|---|---|---|---|
| Relative to α-globin | | | | | | | | | | | | |
| α-globin | 7564 | 100 | 100 | 100 | 100 | 100 | 100 | 100 | 100 | 100 | | |
| Acet/Carb α-globin | 7594 | 0 | 0 | 0 | 1.8 | 1.9 | 5.9 | 5 | 3.9 | 4 | 2.49 | 2.18 |
| αGlc-globin | 7645 | 1.78 | 1.6 | 1.4 | 3 | 2 | 1 | 2.8 | 1.96 | 0.5 | 1.78 | 0.79 |
| α-globin SA adduct | 7671 | 10.9 | 11.2 | 12.6 | 11.6 | 10.6 | 10.7 | 10 | 11.7 | 15 | 11.59 | 1.48 |
| β-globin | 7936 | 70.9 | 53.88 | 85.9 | 93.3 | 89.9 | 99.2 | 84 | 81.2 | 76.4 | 70.18 | 11.93 |
| Relative to β/δ-globin | | | | | | | | | | | | |
| δ-globin | 7921 | 0 | 0 | 0 | 0 | 0 | 0 | 0 | 0 | 0 | | |
| β-globin | 7936 | 100 | 100 | 100 | 100 | 100 | 100 | 100 | 100 | 100 | | |
| δ-globin | 7965 | 3 | 0 | 0 | 5.7 | 2.7 | 6.2 | 9.2 | 5 | 4 | 4.14 | 3.02 |
| γ-globin | 7990 | 0 | 0 | 0 | 0 | 0 | 1 | 1 | 0 | 0 | 0.22 | 0.44 |
| γ-globin | 8005 | 0 | 0 | 0 | 0 | 0 | 0 | 0 | 0 | 0 | 0.00 | 0.00 |
| βGlc-globin | 8017 | 2.56 | 3.4 | 2 | 4.4 | 2.7 | 2.1 | 3.4 | 5.2 | 2.56 | 3.15 | 1.07 |
| β-globin SA adduct | 8039 | 10.25 | 13 | 16.3 | 14 | 13.2 | 11.1 | 13 | 15 | 18.9 | 13.89 | 2.75 |
| ?-globin | 8088 | 2.56 | 2.4 | 0 | 0 | 1.8 | 0 | 0 | 0 | 0 | 0.58 | 1.11 |

Figure 5 (cont.)

B) - Phenotypic abnormal blood samples

| Assigned Peak | m/z | SCD HbS | SCD HbSC | Beta-thalassemia trait | Beta-thalassemia | HbE disease | Alpha-thalassemia trait | Alpha-thalassemia trait | Average | SD |
|---|---|---|---|---|---|---|---|---|---|---|
| Relative to α-globin | | | | | | | | | | |
| α-globin | 7564 | 100 | 100 | 100 | 100 | 100 | 100 | 100 | | |
| Acet/Carb α-globin | 7594 | 2.12 | 1.8 | 2.7 | | 5 | 5.3 | 5 | 3.2 | 2.14 |
| αGlc-globin | 7645 | 1 | 1.8 | 2.2 | 1.98 | 2.5 | 2.4 | 2.7 | 2.1 | 0.57 |
| α-globin SA adduct | 7671 | 13 | 12 | 13.9 | 12.2 | 10.6 | 12.8 | 12.1 | 11.8 | 0.75 |
| β-globin | | 60 | 43.9 | 66.6 | 63.1 | 47.75 | 66.3 | 59 | 58.1 | 8.92 |
| Relative to β/δ-globin | | | | | | | | | | |
| β-globin | 7921 | 100 | 13.4 | 0 | 0 | 0 | 100 | 0 | 0.2 | 2.54 |
| β-globin | 7935 | 0 | 100 | 100 | 100 | 100 | 0 | 100 | 1.7 | 3.12 |
| δ-globin | 7965 | 7.1 | 6.3 | 6.18 | 5.8 | 13.3 | 8.3 | 8.3 | 3.1 | 0.09 |
| γ-globin | 7999 | 0 | 7.7 | 0 | 0 | 0 | 4.5 | 4.5 | 5.1 | 2.78 |
| γ-globin | 8005 | 21.4 | 0 | 6 | 4.7 | 5.80 | 0 | 0 | | |
| βGlc-globin | 8017 | 0 | 9.1 | 12.9 | 12.5 | 13.3 | 3.96 | 6.25 | 13.6 | 1.84 |
| β-globin SA adduct | 8039 | 14.2 | 14.7 | 12.9 | 12.5 | 13.3 | 10.9 | 16.7 | 13.6 | 1.84 |
| γ-globin | 8088 | 7.14 | 7 | 5.6 | 10.3 | 5.6 | 7.5 | 11.6 | 8.7 | 3.89 |

RAPID SCREENING AND EVALUATION OF DIABETES AND PREDIABETES BY GLYCATED HEMOGLOBIN MASS SPECTROMETRY

CROSS-REFERENCE TO RELATED APPLICATIONS

This application is a 35 U.S.C. § 371 national phase application of PCT Application No. PCT/GB15/052487, filed Aug. 27, 2015, which claims priority to Great Britain Application No. 1415369.6, filed Aug. 29, 2014, each of which is incorporated herein by reference in its entirety.

The present invention relates to a method for measuring the levels of non-glycated and glycated hemoglobin within a blood sample using direct mass spectral analysis. The proportion of hemoglobin molecules which are glycated can be used to diagnose pre-diabetes or diabetes.

BACKGROUND

Diabetes and in particular type 2 diabetes, is now a public health issue in the developed and developing worlds. Costly diabetic complications include cardiovascular disease, retinopathy, neuropathy, and nephropathy. Thus, a significant unmet medical needs exist in both detecting and evaluating patients and screening aging populations of a nation for early onset diabetes. For example, in 2011 it was estimated that 25.8 million children and adults in the U.S. (8.3% of the population), have diabetes. While an estimated 18.8 million have been diagnosed with Type 2 diabetes, approximately 7 million are unaware they have the disease. Based on glycaemic measures from 2005-2008, the Centers for Disease Control and Prevention (CDC), reported that 35% of the U.S. adult population had pre-diabetes, that is an estimated 79 million U.S. adults at risk for developing Type 2 diabetes. Similarly in the UK, in 2014, the number of pre-diabetic is claimed to have risen from 11.6% in 2003 to 35.3% in 2013. That is 17.3 Million of UK adults are estimated to have pre-diabetes. In the U.S. alone, the 2007 total annual cost associated with treatment of diabetics was $174 billion. Thus, preventing and managing diabetes and its complications represents a global public health challenge and is a priority for many National healthcare systems.

Detection of diabetes has been traditionally via measurement of glucose levels in blood and urine. For pre-diabetes a glucose tolerance test is taken whereby, following an oral glucose challenge, blood glucose levels are measured, over a timed period, to monitor the maxima and magnitude before levels are brought back to normal. In addition insulin levels can be measured in parallel however the glucose tolerance test requires admittance as a day patient.

Glycated Hemoglobin (Hb) is formed in a non-enzymatic glycation pathway by which hemoglobin's (Hb) reacts freely with blood plasma glucose, even though it is contained within red blood cells. As red blood cells circulate for about 100-120 days in the body, before their components are recycled by the spleen and liver, measurement of glycated Hb therefore reflects the cumulative exposure to glucose: Normal levels of glucose produce a normal amount of glycated hemoglobin; as the average amount of plasma glucose increases, the fraction of glycated hemoglobin increases. Thus, it is a marker for average blood glucose levels over the months prior to the measurement. Rather than a one off test this provides solid evidence of increasing metabolic problems such as pre diabetes. Indeed measurement of glycated Hb provides a much more reliable measure of how well a patient is controlling their diabetes than food and blood glucose diaries.

Thus, a recently favoured test of glycated Hb is the measurement of $HbA_{1C}$ levels, relative to HbA levels. $HbA_{1C}$ is so named because Hb is usually analyzed and measured by elution from reverse phase high pressure liquid chromatography. The chromatographic separation of total Hb resolves the different types of hemoglobin, principally A and A2, from fetal Hb and disease variant of these two types. A minor resolved elution peak is glycated Hb called $HbA_{1C}$. The measurement of $HbA_{1C}$ is the preferred test for diabetes and the onset of metabolic disease as glycated Hb is a cumulative and non-patient compliance dependant test. Point of care testing for $HbA_{1c}$ is recommended by the American Diabetes Association, as it is rapid and allows the clinician to address the patient's status immediately, improving patient compliance. Hemoglobin $A_{1C}$ was recently approved for use as a diagnostic tool, and an $HbA_{1C}$ of greater than or equal to 6.5% is the cut-off point for diagnosis. The pre-diabetic state was cited to be an $HbA_{1C}$>5.7 to 6.4%. The correlation of $HbA_{1C}$ to average glucose concentration was recently validated with patients who have type 2 diabetes mellitus.

However, one diagnostic problem is that $HbA_{1C}$ is not suitable for patients with variant Hb or hemoglobinopathies such as sickle cell trait. This can be because the elution profile of the glycated Hb can be obscured by the elution profile of the variant Hb or it interferes with the differential specificity of $HbA_{1C}$ immunoassays.

A second problem is that, as reported in the WHO 2011 report WHO/NMH/CHP/CPM/11.1, Use of Glycated Hemoglobin ($HbA_{1c}$) in the Diagnosis of Diabetes Mellitus, current $HbA_{1c}$ assays are "unaffordable in most low and middle-income country settings".

The invention describes a rapid robust and affordable method for screening population for diabetes and pre diabetic metabolic syndromes by analyzing blood samples.

The invention describes direct mass spectrographic analysis of a blood sample, which can be lysed and optionally diluted 100-1000 fold in water. The Hb species present in the sample can be resolved by direct mass spectral analysis such as matrix assisted laser desorption time of flight mass spectrometry. The Hb α-globin chain resolved from the glycated species—Hb α-globin Glc, and/or Hb β-globin from Hb β-globin Glc can be measured for example by normalized area under the curve or peak height. Variants of Hb and hemoglobinopathies are resolved and are not influential on the measurement of percentage glycated Hb, as the Hb α-chain and/or Hb β-chain and respective glycated (Glc) orthologos can be used as the differential marker of diabetic glycosylation.

The invention describes a method to help manage and reduce a cause of socio-economic burden on a nation, through early detection and monitoring.

The method describes rapid screening of whole blood samples, such as pin prick samples and blood spot cards, subjected to direct mass spectral analysis, such as MALDI-ToF Mass spectrometry. Analysis may be carried out following lysis, for example in distilled deionized water, or by freezing, and optionally massive dilution at the range of 1/10 to 1/8000 (preferably 1/2000) in for example distilled deionized $H_2O$ or 0.1% trifluoroacetic acid (TFA) in distilled deionised $H_2O$. The resulting spectra is examined as singly charged ions at the Mass/charge range of 15,000 m/z to 16,200 m/z; and/or the doubly charged ions at 7,550 to 8,100 m/z or 7,550 to 8,200 m/z.

Unglycated α-globin is preferably measured at 7,564 m/z
Glycated α globin is preferably measured at 7,645 m/z
Unglycated β-globin is preferably measured at 7,934 m/z
Glycated β-globin is preferably measured at 8,017 m/z The spectra is generated using a matrix, preferably sinapinic acid, and intensity of the characteristic resolved mass peaks of α-globin and glycated α-globin, and/or β-globin and glycated β-globin are measured and a ratio determines the relative percentage glycated globin. The determined relative percentage is indicative of pre-diabetes, diabetes and diabetic patients control of cumulative average blood glucose over the previous 2-3 months.

Thus the invention provides a method of detecting pre-diabetes or diabetes comprising subjecting a blood sample obtained from a subject to direct mass spectral analysis and determining the proportion of glycated hemoglobin (Hb) e.g. glycated α-globin and/or glycated β-globin present in the sample.

"Direct mass spectral analysis" means that the data generated from the mass spectral analysis is used in the method, and not the inferred mass of the components present in the sample.

Pre-diabetes, also referred to as borderline diabetes is usually a precursor to diabetes. It occurs when the blood glucose levels are higher than normal, but not high enough for the patient to be considered to have diabetes. It is often described as the "grey area" between normal blood sugar and diabetic levels. Pre-diabetes may be also be referred to as impaired fasting glucose (IFT), if a patient has higher than normal sugar levels after a period of fasting, or as impaired glucose tolerance (IGT), if a patient has higher than normal sugar levels following eating.

The blood sample can be an untreated sample. Alternatively, the blood sample may be diluted or processed (concentrated, filtered, etc.).

The blood sample can be a whole blood sample collected using conventional phlebotomy methods. For example, the sample can be obtained through venupuncture or as a pin prick sample, such as a finger-stick or heel prick. The blood sample may be a dried blood spot captured on filter paper or other suitable blood spot capture material.

The blood sample is preferably treated to lyse the red blood cells. This can be done by diluting a blood sample in a lysing agent, such as deionized distilled water, preferably at a concentration of 1/1 (i.e. 1 part blood to 1 part lysing agent or distilled deionized water). Alternatively the sample can be frozen to lyse the cells. If the blood sample is a dried blood spot, the blood spot capture material on which the sample is dried can be placed in a lysing agent e.g. distilled deionized water to reconstitute the sample. Alternatively the blood spot can be reconstituted in a suitable buffer prior to lysis.

Preferably the blood sample is diluted preferably after lysis. The blood sample may be diluted 1/10 (i.e. one part sample in 10 parts diluent), 1/500, 1/1000, 1/200, 1/2500, 1/8000 or more. Most preferably the sample is diluted 1/2000 i.e. one part blood sample in 2000 parts diluent. Preferably the diluent is 0.1% trifluoroacetic acid in distilled deionised water, more preferably distilled deionized water.

Preferably the blood sample is not processed between lysis and dilution. In other words the blood sample is only lysed and diluted. Such processing includes concentrating the proteins of interest e.g. Hb, α-globin and/or β-globin; isolating Hb, α-globin and/or β-globin by for example HPLC or treatment with a chemical agent to disrupt or break intramolecular bonds. In particular, the sample is preferably not treated with a reducing agent. More preferably the sample is not treated with dithiothrietol (DTT).

The proportion of glycated α-globin and/or β-globin can be calculated i.e. percentage of α-globin and/or β-globin which is glycated. The percentage is calculated as $$\frac{\text{Glycated globin}}{\text{Total globin (Glycated globin + non-glycated globin)}} \times 100\%$$

A level of ≥4% glycated α-globin and ≥6% β-globin, is indicative of diabetes. A level of 3-4% glycated α-globin and 4-6% glycated β-globin, is indicative of prediabetes. Preferably the proportion of glycated α-globin in calculated in patients with a hemoglobinopathy or a hemoglobinopathy trait.

Methods of generating mass spectra, such as MALDI-Tof MS, are commonly not quantitative technique. For example the Y axis in these spectra is an indicator of "relative strength" of mass peak within the spectra, but not between mass peaks in one sample versus another sample. In order to overcome this, normalization needs to render Y axis value comparable between sample spectra. Thus the spectra obtained from the direct mass spectral analysis is preferably normalized. The spectra is subjected to data processing which results in a normalized statistically determined index of relative proportion of mass spectra. This converts the qualitative mass spectra into a quantitative value. Normalization is the process of producing a data structure to reduce repetition and inconsistencies of data. Several normalization techniques are possible. Typical normalization methods include percentage of total area at a given point, Square difference and ratio of differences. The percentage difference is calculated as Percentage difference=($Y1$-$Y$ref/$Y$ ref×100%)

Wherein Y ref is the minimum Y value of the spectra, and Y1 is Y value for each point.

The square difference is calculated as

Square Difference=$(Y1-Y \text{ ref})^2$

The ratio difference is calculated as

Ratio Difference=(Ratio1−Ratio 2).

Thus the data from the mass spectra is manipulated in order to provide a quantitative measure of the qualitative change shown on the spectra.

Preferably, the spectral model is created by a method of data processing which results in a normalized statistically determined index of relative proportion of mass spectra within a set range. This renders all spectra comparable such that the median and centile variability at any given mass value can be modelled. Preferably the range is between about 7,000-16,500 m/z, more preferably 7,500-16,200 m/z, most preferably 7,500-8,200 m/z. The single charged and/or double charged molecules of globin can be measured. For the singly charged ions, the spectra at the mass/charge range of 15000 m/z to 16200 m/z is examined. For the doubly charged ions, the spectra at the mass/charge range of 6000 to 8100 m/z, more preferably 7550 to 8100 m/z or 7550 to 8200 m/z is examined.

α-globin is preferably measured at 7564 m/z±5 m/z
Glycated α globin is preferably measured at 7645 m/z±5 m/z
β-globin is preferably measured at 7934 m/z±5 m/z
Glycated β-globin is preferably measured at 8017 m/z±5 m/z A normalized statistically determined index of relative proportion of mass spectra within a given range can be calculated from using the total area under the curve of mass spectra. This can then be used to calculate the relative intensity.

The area under the curve of mass spectra is calculated by dividing the mass spectra into a plurality of bins of a given number of m/z. As used herein "Bin" has its usual statistical meaning, for example, of being one of a series of ranges of numerical value into which data are sorted in statistical analysis. For example the bins can be 100 m/z, 50 m/z, 25 m/z, 10 m/z or 5 m/z in size. The smaller the size of the bin used, the more refined the method. Preferably the bin size is 5 m/z.

The relative intensity (Y Axis value) can be calculated by the "square of difference" method and therefore a comparable Y value given for every bin. In this method, the minimum Y value of the spectra (Y ref) was subtracted from the Y value at every bin and the difference was squared. The formula used to calculate square of difference=$(y1-yref)^2$ and the calculated square of difference was then named as "relative intensity".

The relative intensity at each mass bin in a sample can be captured using commercially available statistical tests such as MATLAB®, Stats Direct™ and Origin 8™. The relative intensity for the mass bins for (i) α-globin and glycated α-globin and/or (ii) β-globin and glycated β globin can be used to calculate the proportion of glycated globin present.

Once the spectra has undergone a method of data processing which results in a normalized statistically determined index of relative proportion of mass spectra, the proportion of glycated globin can be determined by measuring the relative height of the peaks corresponding to the glycated and unglycated globins. For the singly charged ions, the spectra at the mass/charge range of 15000 m/z to 16200 m/z is examined. For the doubly charged ions, the spectra at the mass/charge range of 6000 to 8100 m/z, more preferably 7550 to 8200 m/z is examined.

α-globin is preferably measured at 7564 m/z±10 m/z
Glycated α globin is preferably measured at 7645 m/z±10 m/z
β-globin is preferably measured at 7934 m/z±10 m/z
Glycated β-globin is preferably measured at 8038 m/z±10 m/z The analysis of the mass spectra can be easily calculated using a suitable computer software program.

Preferably, the mass spectral analysis carried out is matrix-assisted laser desorption/ionization time-of-flight mass spectrometry (MALDI-ToF MS).

Also described is a method of detecting pre-diabetes or diabetes comprising
a) obtaining a blood sample from a subject;
b) subjecting the sample to direct mass spectral analysis;
c) Calculating the proportion of glycated globin present;
wherein a percentage glycated α globin ≥4% and ≥6% glycated β-globin is indicative of diabetes, and a percentage glycated globin between 3-4% for α-globin and 3-6% for β-globin is indicative of pre-diabetes. Preferably the percentage of glycated globin is the percentage glycated α-globin, in particular in subjects with a hemoglobinopathy.

In this specification, the verb "comprise" has its normal dictionary meaning, to denote non-exclusive inclusion. That is, use of the word "comprise" (or any of its derivatives) to include one feature or more, does not exclude the possibility of also including further features. The word "preferable" (or any of its derivatives) indicates one feature or more that is preferred but not essential.

All or any of the features disclosed in this specification (including any accompanying claims, abstract and drawings), and/or all or any of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The application will now be described in the examples below which refer to the following figures.

FIG. 5—A table of calculated relative amounts of glycated α-globin and β-globin and other globin molecules in 9 adults and 7 patients with various hemoglobinopathies

EXAMPLE 1

Method
Sample Processing

The optimal dilution for whole blood or dried blood spot is between 1/1000 and 1/2000 in either ddH$_2$O or 0.1% TFA in ddH$_2$O after an initial lysis of sample with ddH$_2$O (1:1 v/v). This dilutional step effectively purifies the Hb from other components of blood for mass spectral analysis as Hb is the most abundant protein. In addition the dilution in ddH$_2$O (of 0.1% TFA/ddH$_2$O) dissociates the constituent globin proteins for resolved analysis by MALDI-ToF Mass spectrometry.

Dilutions higher than 1/8000 results in progressively weaker mass spectral signal.

MALDI ToF Mass Spectral Analysis

The optimal matrices are sinnapinic acid (SA), ferulic acid (FA) and alpha 4-cyano hydroxycinnamic acid (CHCA). Sinapinic acid being the preferred matrix mixed or as pre-coating layer to a mixed drop of 1/1000 to 1/8000 diluted sample (optimal 1/2000).

Steel MALDI plates (384 wells) were prepared by pipetting 0.5 µl of matrix solution (sinapinic acid—20 mg/ml dissolved in 50/50 v/v acetonitrile (ACN)/ddH$_2$O and 0.1% trifluoacetic acid (TFA)) and allowed to dry. 0.5 µl of sample, was mixed with SA and spotted on the dry matrix. This was allowed to dry at room temperature for 1 hour before MALDI TOF MS analysis.

The mass spectrometric analysis was carried out using a Shimadzu Axima plus MALDI mass spectrometer: the pulse nitrogen laser ($\lambda_{max}$=337 nm), was fired at 75 to 80% arbitrary units of power. The ions were accelerated by a 20 kV electrical field down a 1.2 m linear tube and detected by a micro-channel plate detector at a sampling rate of 500 MHz. Spectra were generated by summing 20-30 laser shots. A positive linear mode with delayed extraction was used in order to acquire the spectra.

The instrument was internally calibrated whereby a 1/1000 diluted sample of blood was spiked with 10 pmoles/ul Cytochrome C (1:2, v/v) The two points calibration generated was at [M+H]+=12 361 m/z and [M+2H]2+=6181 m/z A mass spectral region of between 6,000 and 17,000 m/z was collected and analyzed and in particular the range of 7500 to 8200 m/z examined for doubly charged globin proteins.

These are characterized both in respect to centroid mass assignment and relative peak intensity either as comparative normalized peak height or normalized peak area in the spectral range examined.

Results

Figure 1:
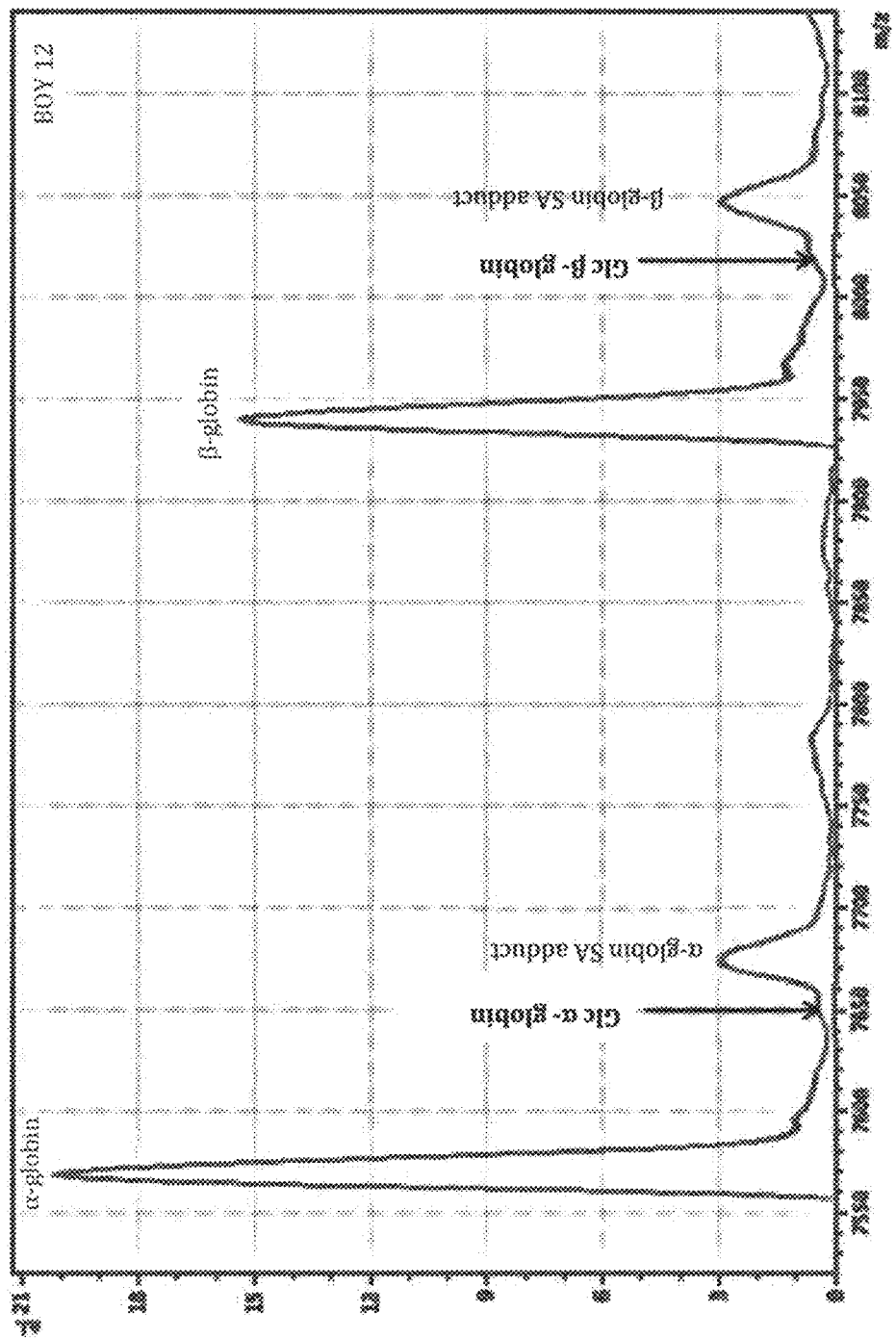
FIG. 1 shows a spectra of normal blood in a 12 year old male

FIG. 1 spectra of blood globins from a boy of 12 years.

A blood sample from a normal male child of 12 years demonstrated a spectra with clearly evident peaks corresponding to α and β globin and corresponding matrix (sinnapinic acid—SA) adducts (see FIG. 1 and table 1). Other globin adducts and other globins (δ, Gγ, Aγ and ε) are barely detected (see table 1). Furthermore glycated α and β-globin orthologs were barely visible (indicated in FIG. 1) at <1% of the parent globin.

Figure 2:
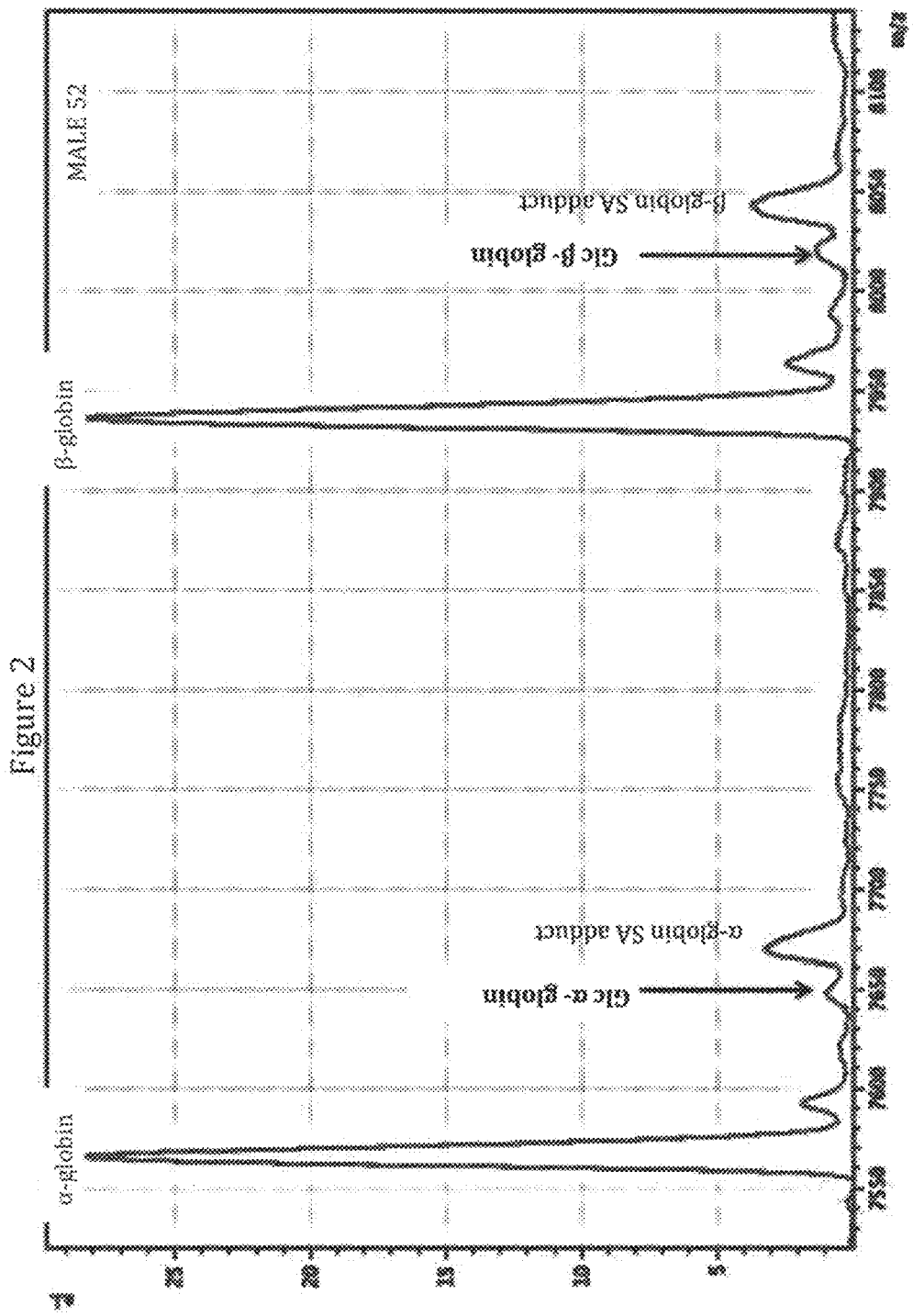
FIG. 2 shows a spectra of normal blood in an obese 52 year old male

FIG. 2 spectra of blood globins from a 52 year old man.

A normal but obese adult blood sample reveals peaks for α-globin and β-globin along with their associated SA adducts. In addition elevated δ-globin is noted along with other α and β-globin adducts, whilst other globins (Gγ, Aγ and ε) are barely detected (see FIG. 2 and table 1). The blood sample revealed glycated α-globin and β-globin peaks representing 3% and 5% of the parent globins.

Figure 3:
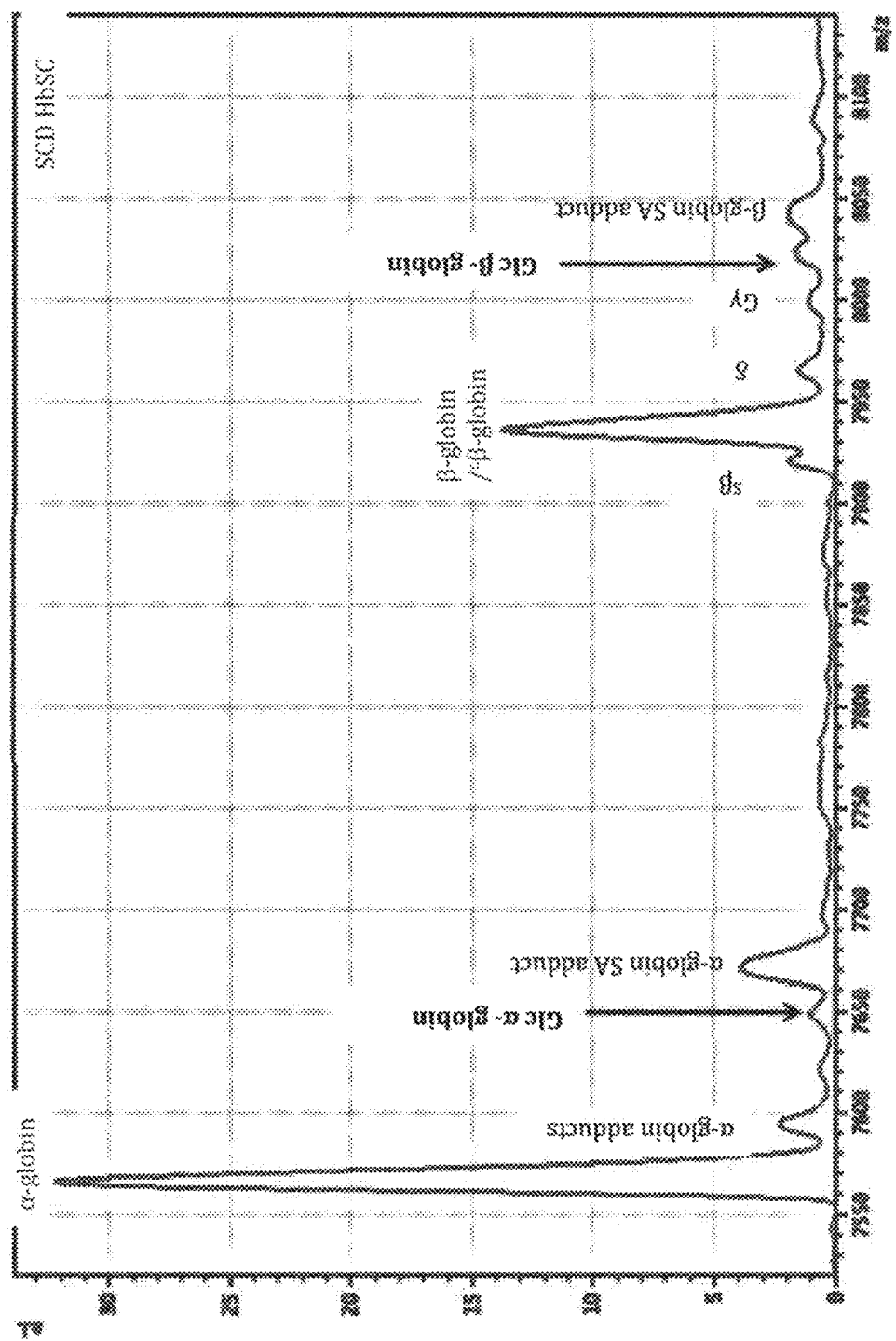
FIG. 3 shows a spectra of blood in a patient with sickle cell disease HbSC

FIG. 3 spectra of blood globins from a patient with Hb SC—Sickle cell diseases.

Blood sample from a patient with sickle cell disease (HbSC) FIG. 3 revealed normal and glycated α-globin peaks and a peak for $^S\beta$ at 7920 m/z clearly resolved from β-globin at 7934 m/z and $^C\beta$ approx. 7933 m/z. Baseline elevation of δ and Gγ globins at 7965 and 7996 m/z was evident as was a new peak at 8023 m/z. The blood sample revealed normal and glycated α-globin peaks and the % comparison of intensity was 1.8% whilst the glycated β-globin was 6.3% of the parent β-globin.

Figure 4:
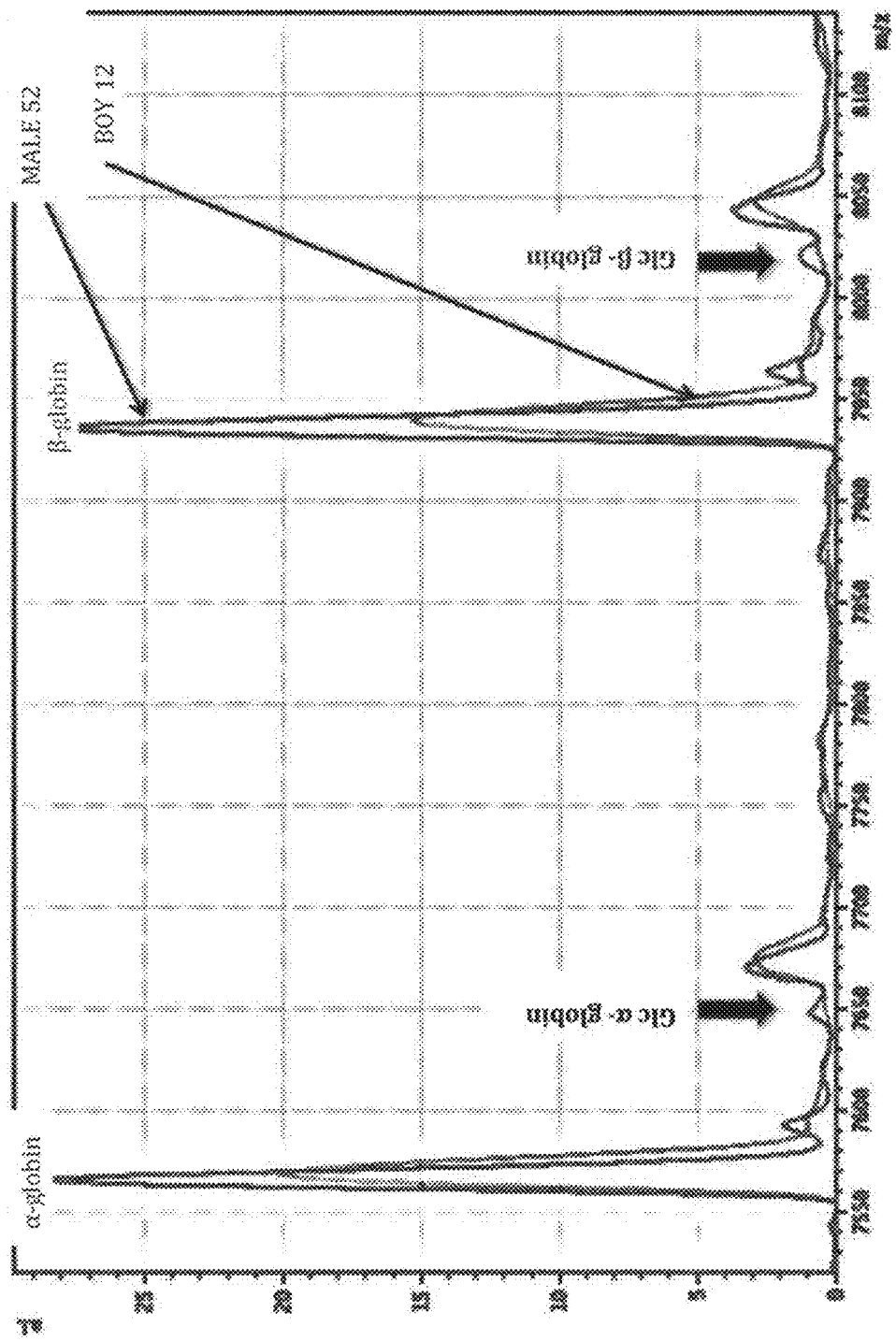
FIG. 4 shows an overlay of the 12 year old boy and 52 year old male blood spectra.

FIG. 4 Comparison of blood globins of a 52 year old male and a 12 year old boy.

Superimposing the 52 year old adult male blood spectra over the spectra from the 12 year old boy's, illustrates the elevation in circulating glycated α and β globins in the adult sample (FIG. 4).

FIG. 5 Tabulated comparison of 9 adult spectra peak intensities with that from 7 assorted hemoglobinopathy patients.

Glycated α-chain was detected in all samples and was clearly resolved in phenotypically normal samples and those with hemoglobinopathies, including sickle cell disease. Glycated β-globin was clearly distinguishable in all normal samples, but compromised by fetal globin expression which was generally elevated in all hemoglobinopathies (FIG. 5). Expressed as a percentage of the α-globin intensity, the glycated ortholog represented between 0.5 and 3% (mean 1.78%, SD 0.79%) for phenotypic normal adults; and between 1 and 2.7% (mean 2.1, SD 0.57%) for those with hemoglobinopathies, including carriers. Expressed as a percentage of the β-globin intensity, the glycated ortholog represented between 2 and 5.2% (mean 3.15%, SD 1.07%) for phenotypic normal adults; and between 0 and 9.1% (mean 5.1%, SD 2.78%) for those with hemoglobinopathies including carriers (see FIG. 5).

Discussion

Elevated Glycation of Hemoglobin is associated with poor regulation of blood glucose. HbA1c was first identified as a chromatographic fraction of Hemoglobin in 1971 and characterized as a measure of the beta-N-1-deoxy fructosyl component of hemoglobin. Normal levels of glucose produce a normal amount of glycated hemoglobin. As the average amount of plasma glucose increases, the fraction of glycated hemoglobin increases in a predictable way. This serves as a marker for average blood glucose levels over the previous 3 months prior to the measurement as this is the half-life of red blood cells.

In diabetes mellitus, higher amounts of glycated hemoglobin, indicating poorer control of blood glucose levels, have been associated with cardiovascular disease, nephropathy, and retinopathy. Monitoring HbA1c in type 1 diabetic patients has been adopted as a measure to improve outcomes. Several methods to measure "HbA1c" including HPLC, immunoassay and capillary electrophoresis are in clinical use. Largely regarded as a measure of β-globin glycation, its measurement is compromised by fetal β-like globin expression and with β-globin gene mutations such as in sickle cell disease and beta-thalassemia, and carriers of such mutation. However, elevated glycation has recently been shown to be associated with such hemoglobinopathies and may reflect an increased chemical susceptibility to glycation in such affected blood cells.

The present method clearly resolves the glycated forms of α- and β-globin from each other and their respective non-glycated parents. This gives a finer discrimination of the glycation of hemoglobin and is not compromised by the presence of a mutation or aberrant globin gene expression that adversely affects other methods to measure Hb glycation.

conclusion

MALDI-Tof MS spectral analysis of drop or dried spot whole blood, following 1/2000 dilution in ddH2O reveals resolved globin proteins and clear resolution of glycated orthologo of α and β globins. Comparison of signal intensity of the glycated α-globin peak to the parent α-globin peak represents a rapid and economic screening and monitoring testing method for diabetes and pre-diabetes.

TABLE 1

Identification of Globins - The best resolution was achieved in the m/z range 7500 to 8100 corresponding to $[M = 2H]^{2+}$ ions.

| Peak assignment to Globin chains | M/Z of $[M = 2H]^{2+}$ |
|---|---|
| A | 7564 m/z, ±5 m/z |
| Acetyl and Carbonyl adducts of α-globin | 7594 m/z, ±5 m/z |
| Glycated α | 7645 m/z, ±5 m/z |
| Matrix (SA) adduct of α-globin | 7671 m/z, ±5 m/z |
| $^s\beta$ | 7921 m/z |
| B | 7936 m/z, ±5 m/z |
| Δ | 7965 m/z, ±5 m/z |
| Gγ | 7996 m/z, ±5 m/z |
| Aγ | 8005 m/z, ±5 m/z |
| Glycated β | 8017 m/z, ±5 m/z |
| Matrix (SA) adduct of β-globin | 8039 m/z ±5 m/z |
| Marker 8088 m/z possibly ε-globin | 8088 m/z ±5 m/z |

The invention claimed is:

1. A method of detecting prediabetes or diabetes comprising subjecting a blood sample obtained from a subject to direct mass spectral analysis and determining the proportion of glycated hemoglobin (Hb) present in the sample, wherein the sample subjected to direct mass spectral analysis is not processed other than lysis and/or dilution, and wherein determining the proportion of glycated hemoglobin comprises measuring the levels of doubly charged hemoglobin or globin molecules.

2. The method according to claim 1 wherein determining the proportion of glycated hemoglobin present comprises measuring (i) the levels of glycated α globin and unglycated α globin and/or (ii) the levels of glycated β globin and unglycated β globin.

3. The method according to claim 1, wherein the blood sample is lysed prior to said direct mass spectral analysis.

4. The method according to claim 1, wherein the blood sample is diluted prior to direct mass spectral analysis.

5. The method according to claim 1, wherein the spectra obtained from the direct mass spectral analysis is normalised.

6. The method according to claim 5, wherein the amount of glycated Hb and unglycated Hb is measured using the peak height of the mass spectra obtained from the direct mass spectral analysis.

7. The method according to claim 1, wherein the proportion of glycated hemoglobin is calculated as the percentage glycated hemoglobin.

8. The method according to claim 1 wherein the spectra obtained from the direct mass spectral analysis is examined in the range 7,000 to 16,500 m/z.

9. The method according to claim 1, wherein the spectra obtained from the direct mass spectral analysis is examined in the range 6,000 to 8,100 m/z.

10. The method according to claim 1, wherein the amount of glycated Hb and unglycated Hb is measured using the total area under the curve of the mass spectra obtained from the direct mass spectral analysis.

11. The method according to claim 1, wherein a percentage of glycated α-globin between 3-4% and/or a percentage of glycated β-globin between 3-6% is indicative of pre-diabetes.

12. The method according to claim 1, wherein a percentage glycated α globin ≥4% and/or a percentage glycated β-globin ≥6% is indicative of diabetes.

13. The method according to claim 1, wherein the mass spectral analysis carried out is matrix-assisted laser desorption/ionization spectrometry (MALDI).

14. The method according to claim 13, wherein the MALDI spectrometry is time-of-flight mass spectrometry (MALD-ToF MS).

15. A method of detecting prediabetes or diabetes comprising subjecting a blood sample obtained from a subject to direct mass spectral analysis and determining the proportion of glycated hemoglobin (Hb) present in the sample, wherein the sample subjected to direct mass spectral analysis is not processed other than lysis and/or dilution; wherein the spectra obtained from the direct mass spectral analysis is examined in the range 6,000 to 8,100 m/z and determining the proportion of glycated hemoglobin comprises measuring the levels of the doubly charged hemoglobin or globin molecules.

\* \* \* \* \*